United States Patent
Enniss

(10) Patent No.: US 11,883,034 B2
(45) Date of Patent: Jan. 30, 2024

(54) CLIP CARTRIDGE

(71) Applicant: TELEFLEX MEDICAL INCORPORATED, Morrisville, NC (US)

(72) Inventor: Ian Enniss, Morrisville, NC (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 270 days.

(21) Appl. No.: 17/321,082

(22) Filed: May 14, 2021

(65) Prior Publication Data
US 2021/0267604 A1   Sep. 2, 2021

Related U.S. Application Data

(63) Continuation of application No. PCT/US2019/061763, filed on Nov. 15, 2019.

(60) Provisional application No. 62/768,640, filed on Nov. 16, 2018.

(51) Int. Cl.
*A61B 17/122* (2006.01)
*A61B 17/128* (2006.01)

(52) U.S. Cl.
CPC ...... *A61B 17/1222* (2013.01); *A61B 17/1285* (2013.01)

(58) Field of Classification Search
CPC ............... A61B 17/1222; A61B 50/33; A61B 2050/3008; A61B 50/30; A61B 17/122; A61B 17/064; A61B 17/083; A61B 17/105; A61B 17/10; B65D 83/00; B65D 85/00

USPC ........................................ 606/142, 143, 157
See application file for complete search history.

(56) References Cited

U.S. PATENT DOCUMENTS

| 4,296,751 | A | 10/1981 | Blake, III et al. | |
| 6,419,682 | B1* | 7/2002 | Appleby | A61B 17/1222 206/339 |
| 2004/0040875 | A1* | 3/2004 | Gallagher | A61B 17/1222 206/399 |
| 2006/0124485 | A1* | 6/2006 | Kennedy | A61B 17/1222 206/340 |
| 2012/0029533 | A1 | 2/2012 | Whitfield et al. | |
| 2012/0029534 | A1 | 2/2012 | Whitfield et al. | |

(Continued)

OTHER PUBLICATIONS

International Search Report and Written Opinion issued in PCT/US2019/061763, dated Jan. 13, 2020.

*Primary Examiner* — Kathleen S Holwerda
*Assistant Examiner* — Serenity A Miller
(74) *Attorney, Agent, or Firm* — BakerHostetler

(57) ABSTRACT

A cartridge may include a pair of side walls separated by a compartment, the compartment being configured to receive a surgical clip, and a base member supporting the pair of side walls. The pair of side walls may extend at an acute angle relative to a vertical axis of the base member to hold the surgical clip at the acute angle. The acute angle may be greater than 10° and/or about 20-30°. The cartridge may also include a pedestal extending between the pair of side walls and configured to support the surgical clip, where the pedestal is disposed at the acute angle. The cartridge may further include a retainer configured to retain the surgical clip in the compartment, the retainer including a pair of fingers configured to contact the surgical clip, where the pair of fingers are oriented at the acute angle.

30 Claims, 5 Drawing Sheets

(56) References Cited

U.S. PATENT DOCUMENTS

2012/0048759 A1* 3/2012 Disch ................. A61B 17/1222
 206/339
2014/0054192 A1 2/2014 Chancibot

* cited by examiner

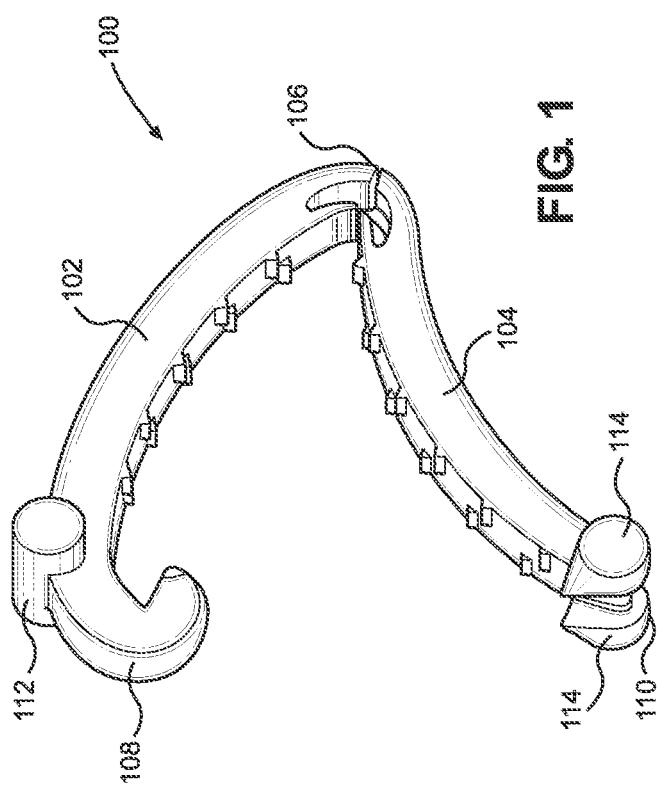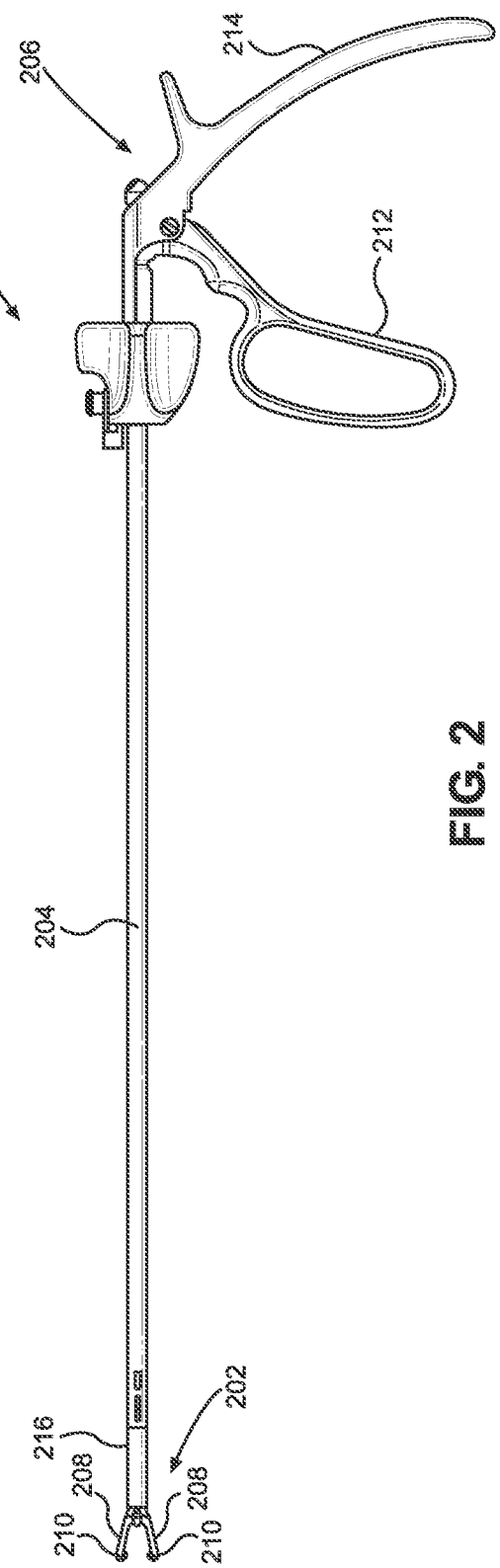
FIG. 1
FIG. 2

CLIP CARTRIDGE

PRIORITY

This patent application is a continuation of International Patent Application No. US19/61763 (filed Nov. 15, 2019), which claims priority to U.S. Provisional Patent Application No. 62/768,640 (filed on Nov. 16, 2018), the entire disclosures of which are expressly incorporated herein by reference.

TECHNICAL FIELD

The present invention relates generally to cartridges, and more particularly, to cartridges for retaining surgical clips at an angled orientation.

BACKGROUND

Ligation of tissue (e.g., blood vessels, lymph nodes, nerves, cystic ducts, and cardiac tissue) is a common practice for many surgical procedures. The procedure is often performed with a manual clip applier that loads a surgical clip from a cartridge and applies the surgical clip to the tissue. The surgical clips are relatively quick to apply to tissue. The cartridge can be placed on a surface during the procedure and accessed to load a surgical clip onto the clip applier when needed. Accordingly, the use of surgical clips and cartridges in endoscopic and open surgical procedures have grown dramatically.

The present inventor recognizes that there is a need to improve one or more features of the cartridges, such as the visibility of the surgical clip and/or the comfort of the user during loading the clip applier. Loading surgical clips onto the clip applier from current cartridges can be difficult because of the relative small size of the surgical clips. Proper loading requires alignment of jaws of the clip applier along the length of each surgical clip and sufficient engagement of the jaws to interfaces on legs of the surgical clips. Insufficient engagement of the surgical clip can result in the surgical clip falling out of the jaws and/or being improperly applied to tissue. The inventor recognizes that one cause of this shortcoming is that the clip applier eclipses the surgical clip in current clip appliers during loading when viewed from above. For example, when the cartridge is placed on the surface of a table and the jaws are vertically inserted into the cartridge, the clip applier and/or a hand of the user often blocks visibility of the surgical clip in the cartridge and at least partially prevents the user from viewing the engagement of the clip applier with the surgical clip. This can lead the user to solely rely on tactile and/or audible feedback to determine if the surgical clip is loaded into the clip applier. The vertical loading of the clip applier may also not be a physically natural motion for some users. The disclosed devices and methods are directed to mitigating or overcoming one or more of the problems set forth above and/or other problems in the prior art.

A first aspect of the present invention is directed to a cartridge. The cartridge may include a pair of side walls separated by a compartment, where the compartment is configured to receive a surgical clip. The cartridge may also include a base member supporting the pair of side walls. The pair of side walls may extend at an acute angle relative to a vertical axis of the base member, such that the cartridge retains the surgical clip at the acute angle.

In some embodiments, the side walls are substantially parallel. In some embodiments, the acute angle is greater than 10°. In some embodiments, the acute angle is about 20-30°. In some embodiments, the cartridge further includes a pedestal extending between the pair of side walls and configured to support the surgical clip, where the pedestal is disposed at the acute angle relative to the vertical axis of the base member. In some embodiments, the cartridge may further include a pair of rails extending longitudinally along the base member, where the pair of rails have a sawtooth configuration with inclined segments at the acute angle relative to the vertical axis of the base member. In some embodiments, the cartridge further includes a retainer configured to retain the surgical clip in the compartment, the retainer including a pair of fingers configured to contact the surgical clip and the pair of fingers are oriented at the acute angle in some embodiments, the retainer further includes a pair of longitudinal portions supporting the pair of fingers, where the longitudinal portions have a sawtooth configuration with inclined segments at the acute angle. In some embodiments, the pair of rails receive the pair of longitudinal portions of the retainer. In some embodiments, at least one of the side walls has a surface inclined at a surface angle toward the compartment, the surface angle being acute relative to a vertical axis of the at least one of the side walls. In some embodiments, the surface angle is about 5-45° relative to the vertical axis of the at least one of the side walls. In some embodiments, the cartridge has more than a pair of walls along a longitudinal axis of the base member, and a plurality of the compartments between respective pairs of walls. In some embodiments, the base member includes a pair of longitudinal walls extending on opposing sides of the compartment.

A second aspect of the present disclosure is directed to a cartridge. The cartridge may include a cartridge body having a pair of side walls separated by a compartment, the compartment being configured to receive a surgical clip, a base member supporting the pair of side walls, a pedestal extending between the pair of side walls and configured to support the surgical clip, and a pair of rails extending longitudinally along the base member. The cartridge may also include a retainer including a pair of fingers configured to contact the surgical clip, the retainer having a pair of longitudinal portions disposed on the pair of rails. The pair of side walls and the pedestal may extend at an acute angle relative to a vertical axis of the base member, such that the cartridge retains the surgical clip at the acute angle.

In some embodiments, the pair of side walls are substantially parallel in some embodiments, the acute angle is greater than 10°. In some embodiments, the acute angle is about 20-30° In some embodiments, the pair of rails have a sawtooth configuration with inclined segments at the acute angle. In some embodiments, the pair of fingers are oriented at the acute angle. In some embodiments, the longitudinal portions have a sawtooth configuration having inclined segments at the acute angle.

BRIEF DESCRIPTION OF THE DRAWINGS

In order that the invention may be readily understood, aspects of this invention are illustrated by way of examples in the accompanying drawings.

FIG. 1 illustrates an exemplary embodiment of a surgical clip, according to the present invention.

FIG. 2 illustrates an exemplary embodiment of a clip applier, according to the present invention.

DETAILED DESCRIPTION

Figure 3:
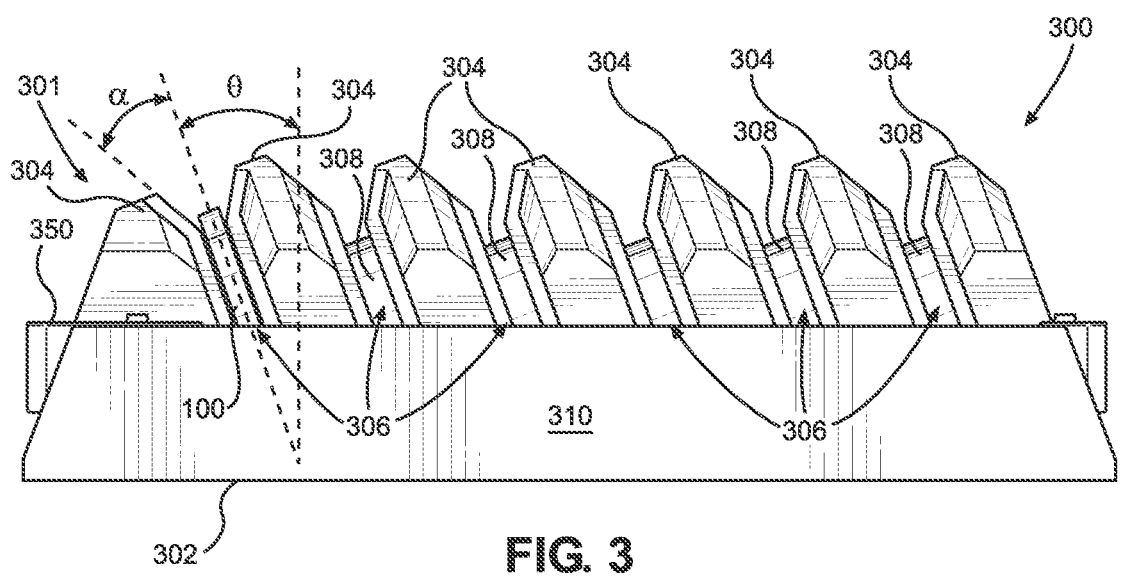
FIG. 3 illustrates a side view of an exemplary embodiment of a cartridge loaded with the surgical clip of FIG. 1, according to the present invention.
Figure 4:
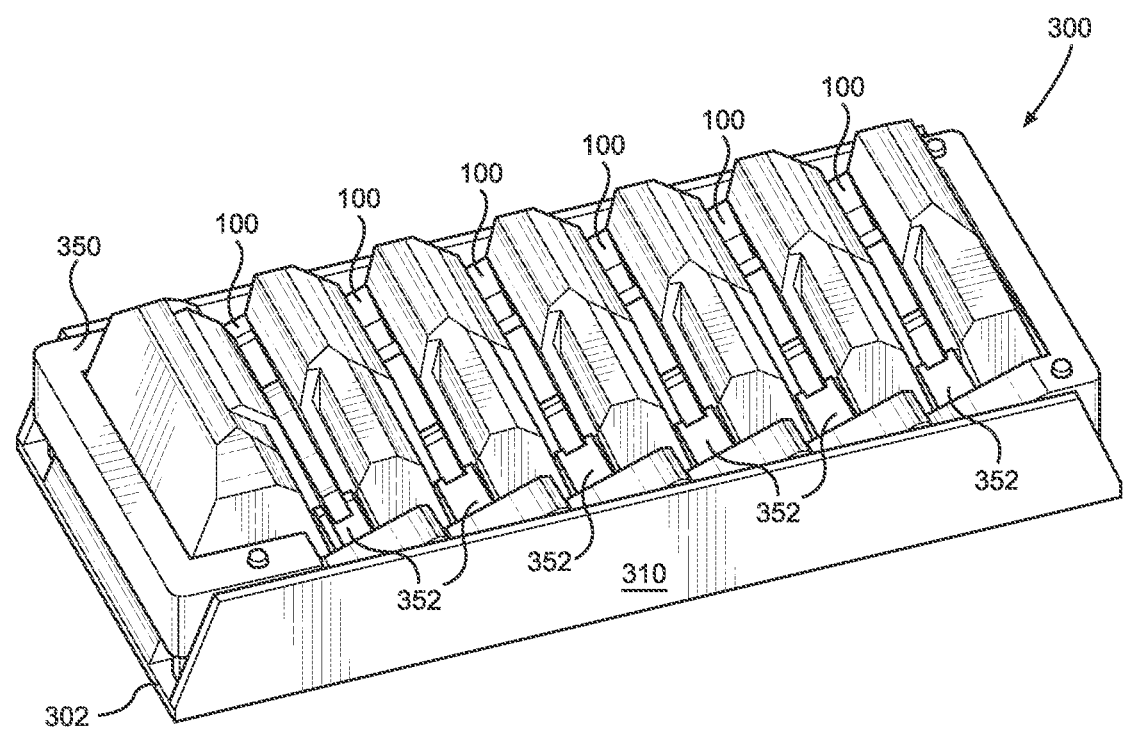
FIG. 4 illustrates a perspective view of the exemplary embodiment of the cartridge of FIG. 3 loaded with a plurality of the surgical clips of FIG. 1, according to the present invention.
Figure 5:
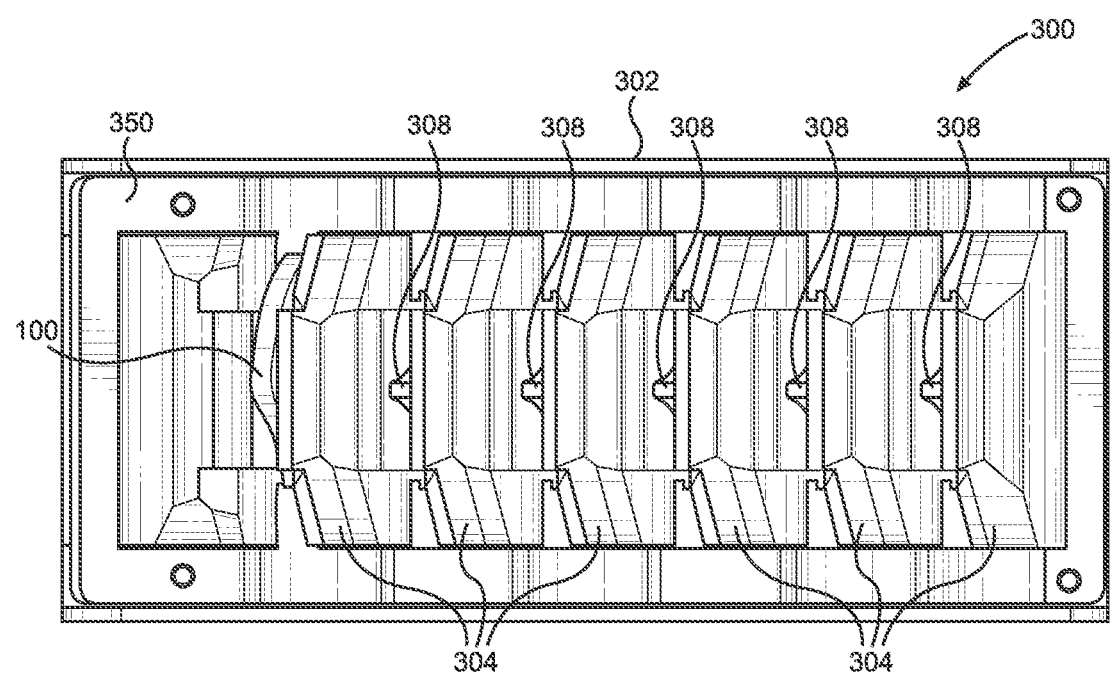
FIG. 5 illustrates atop view of the exemplary embodiment of the cartridge of FIGS. 3 and 4 loaded with the surgical clip of FIG. 1, according to the present invention.

The invention will now be described with reference to the figures, in which like reference numerals may refer to like parts throughout. The present invention is generally directed to a cartridge configured to store one or more surgical clips in an angled configuration to facilitate loading of a clip applier. In order to make it easier for a user to load the surgical clip into the clip applier properly, the present invention provides a cartridge having, among other things, compartments at a non-zero acute angle, θ, from a vertical axis of a base member. The acute angle of the compartments allows the user to bring jaws of a clip applier to the cartridge at a more comfortable angle and improves visibility of the interface between the jaws and the cartridge. In that sense, the clip applier and/or a hand of the user does not block visibility of the surgical clip during loading, especially when the user is looking at the cartridge from above. The cartridge may also be rotated 180° when placed on a supporting surface (e.g., a table) to accommodate a right-handed or left-handed user. The acute angle may be greater than 10° from the vertical axis of the base member in some embodiments, but an optimal angle may be about 20-30° to provide the most comfortable angle for the user and to ensure visibility of the surgical clip. The cartridge may include wider compartments defined by side walls with recessed and/or angled surfaces, improving visibility especially in low-light conditions. For example, at least one of the side walls for each compartment may include an angled upper surface leading into the compartment to further enhance visibility. The angled surfaces of the side walls may also physically guide the applier jaws into the compartment to engage the surgical clip. The side walls may also have recessed shoulders extending at an angle along the surgical clip that lower corners of the walls to further provide visibility of the interfaces at the ends of the surgical clip when looking down at the cartridge.

FIG. 1 illustrates an exemplary embodiment of a surgical clip 100. The surgical clip 100 may include a first leg member 102 and a second leg member 104 pivotally coupled at a hinge portion 106. The surgical clip 100 may include one or more latching or locking mechanisms. For example, the first leg member 102 may include a distal end portion having a hook member 108, and the second leg member 104 may include a distal end portion having a tip member 110. The first leg member 102 and/or the second leg member 104 may be configured to be pivoted relatively to each other between an open configuration and a closed configuration at the hinge portion 106. The leg members 102, 104 may be curved, such that the first leg member 102 may have a concave inner surface, and the second leg member 104 may have a convex inner surface. The leg members 102, 104 may be configured to flex for the hook member 108 to extend around the tip member 110 to lock and/or latch the surgical clip 100 in the closed configuration. The surgical clip 100 may further include one or more interface portions. For example, the first leg member 102 may include one or more bosses 112 on the distal end portion proximal of the hook member 108, and the second leg member 104 may include one or more bosses 114 on the distal end portion at the tip member 110. The one or more bosses 112, 114 may secure to a clip applier 200 during loading and/or application of the surgical clip 100 to tissue. Exemplary embodiments of the surgical clip 100 are further disclosed in U.S. Pat. Nos. 5,100,416 and 9,445,820, the entire disclosures of which are incorporated herein by reference.

FIG. 2 illustrates an exemplary embodiment of the clip applier 200. The clip applier 200 may include a jaw mechanism 202 pivotally connected to a distal end of a shaft 204 and a handle mechanism 206 connected to a proximal end of the shaft 204. The jaw mechanism 202 may include first and second jaw members 208 pivotally connected to the distal end of the shaft 204. The jaw members 208 may include one or more recesses 210 configured to receive the bosses 112, 114 to releasably retain the surgical clip 100 during application. The handle mechanism 206 may include an actuating member 212 configured to actuate the jaw members 208 between open and closed configurations. For example, pivoting of the actuating member 212 relative to a stationary handle member 214 of the handle mechanism 206 may cause longitudinal movement of an actuating rod (not shown) through the shaft 204 and/or a cam tube 216 at a distal end of the shaft 204 to pivot the jaw members 208 between open and closed configurations to apply the surgical clip 100 to tissue.

Figure 6:
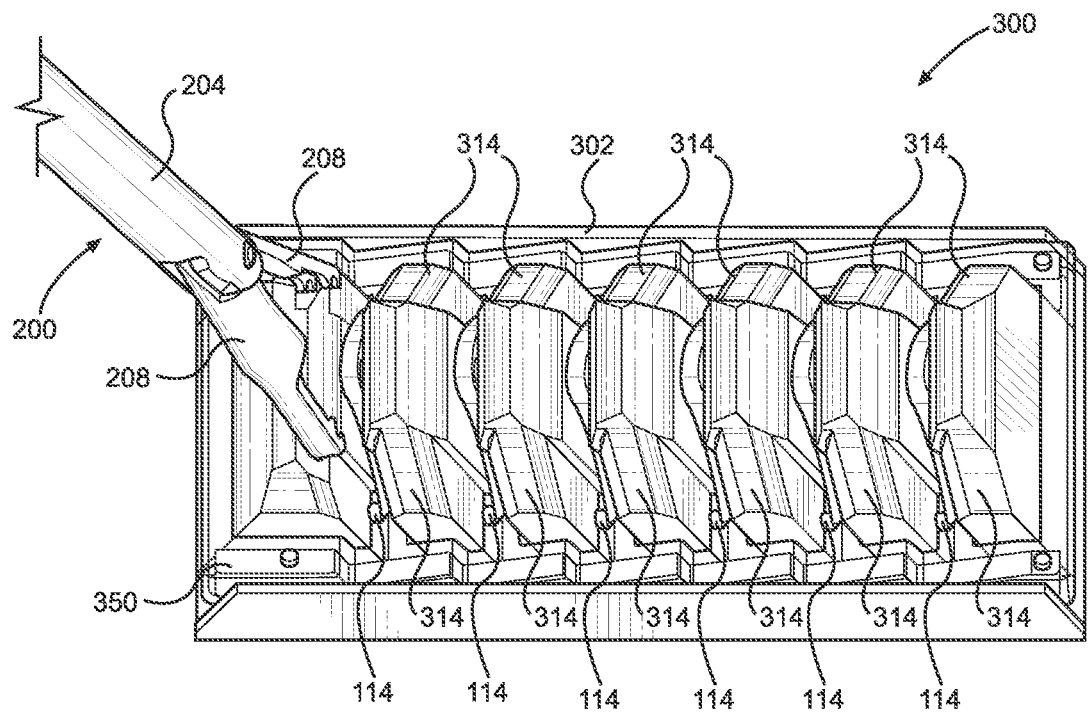
FIG. 6 illustrates atop view of the clip applier of FIG. 2 loading the surgical clip of FIG. 1 from the exemplary embodiment of the cartridge of FIGS. 3-5.
Figure 7:
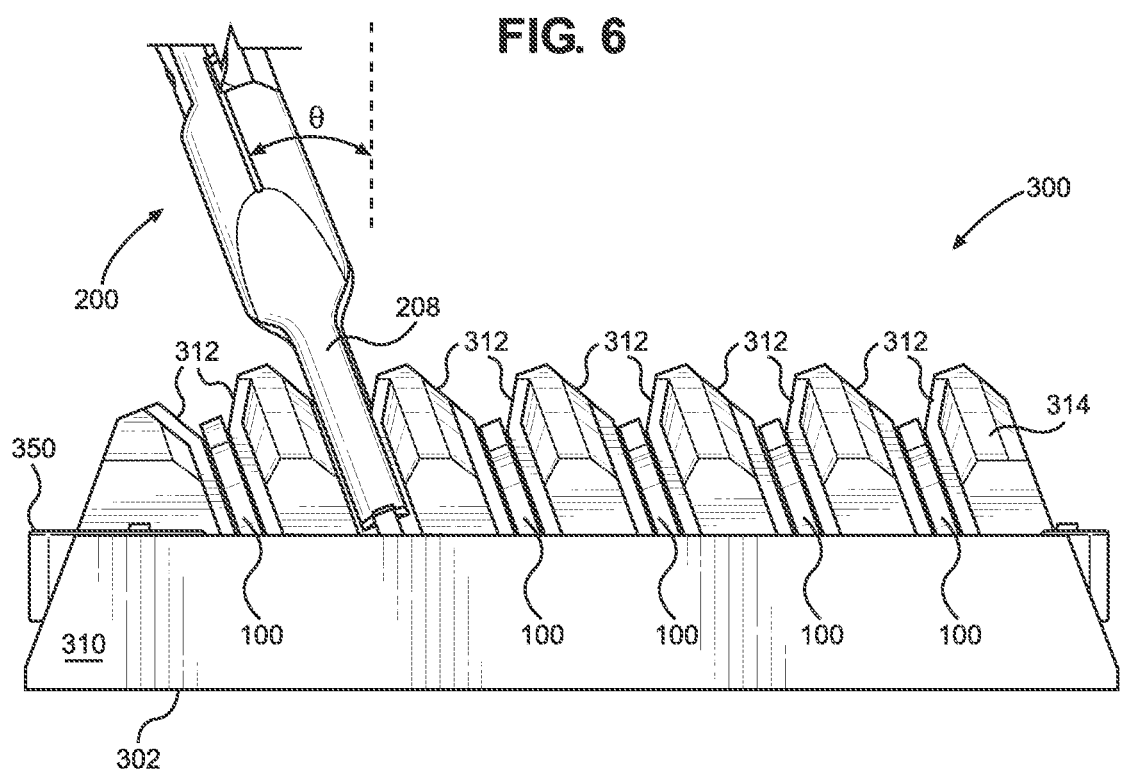
FIG. 7 illustrates a side view of the clip applier of FIG. 2 loading the surgical clip of FIG. 1 from the exemplary embodiment of the cartridge of FIGS. 3-6.
Figure 8:
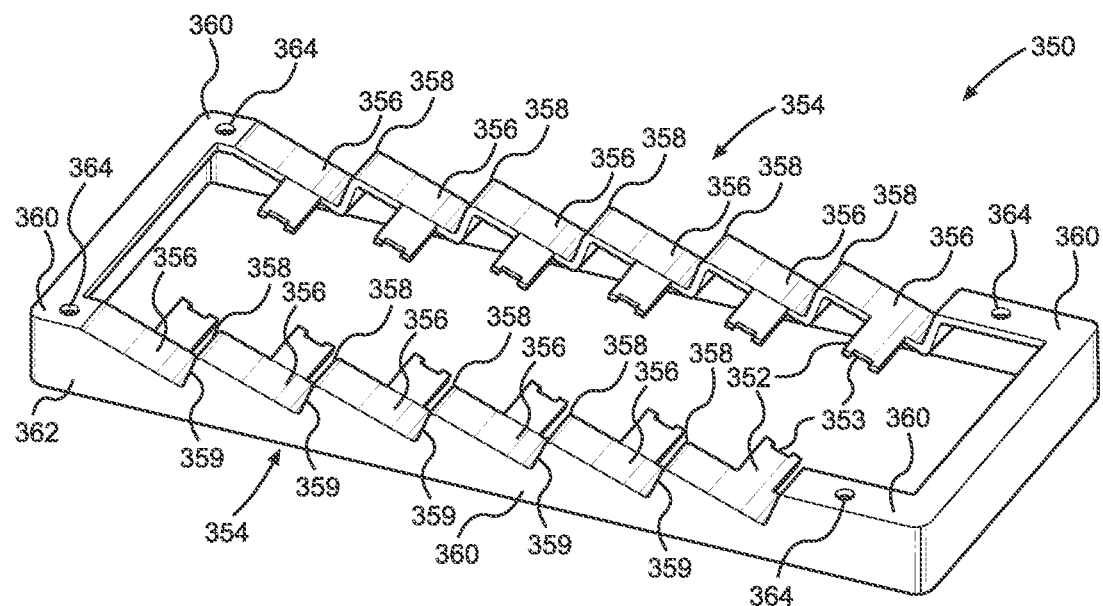
FIG. 8 illustrates a perspective view of an exemplary embodiment of a retainer of the cartridge of FIGS. 3-7.
Figure 9:
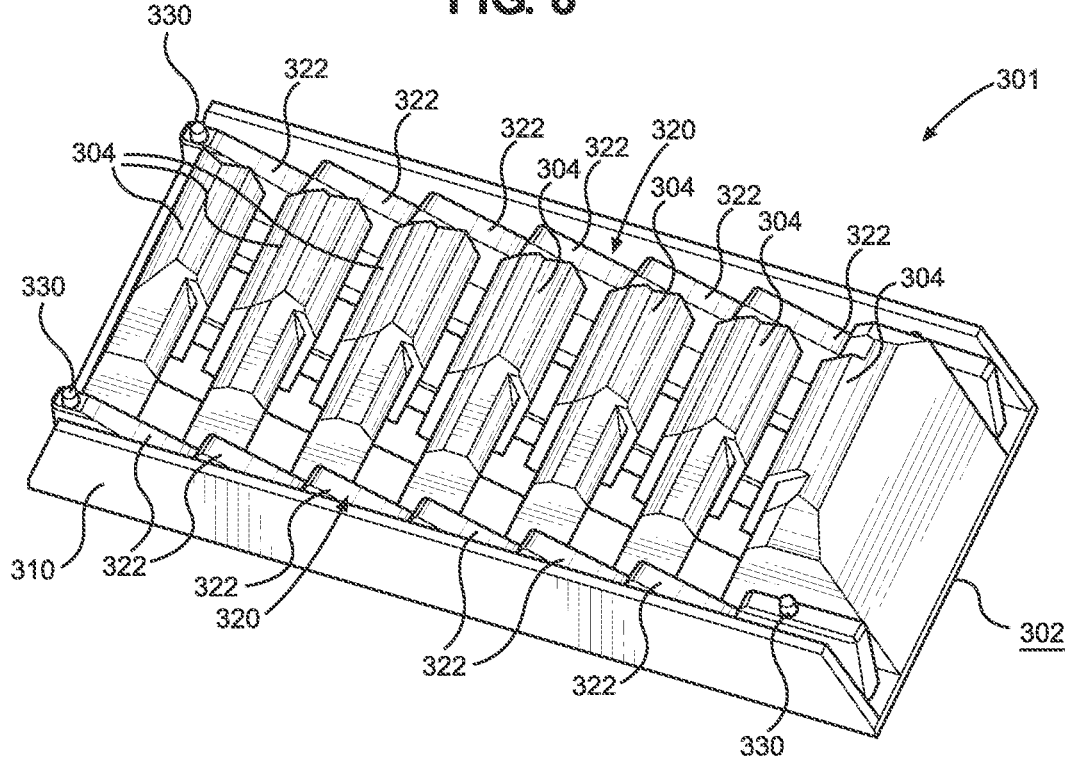
FIG. 9 illustrates a perspective view of an exemplary embodiment of a cartridge body of the cartridge of FIGS. 3-8.

FIGS. 3-9 illustrate an exemplary embodiment of a cartridge 300 that may be loaded with one or more of the surgical clips 100. The cartridge 300 may have a cartridge body 301 and a retainer 350. The cartridge body 301 may include a plurality of side walls 304 defining one or more compartments 306 therebetween. The one or more compartments 306 may retain one or more of the surgical clips 100 at a non-zero acute angle, θ, in a stored configuration, defined by the orientation of the longitudinal axis of the surgical clips 100 relative to a vertical axis of the base member 302. The one or more compartments 306 may receive the jaw members 208 to load the surgical clip 100 onto the clip applier 200, as illustrated in FIGS. 6-7.

The plurality of side walls 304 may extend from the base member 302 and be separated by the compartments 306 in a pairwise manner. The cartridge body 301 may include a plurality of pedestals 308 extending between pairs of the side walls 304 to support the surgical clip 100. The side walls 304 may extend substantially parallel from the base member 302 and have vertical axes disposed at the acute angle, θ, relative to the vertical axis of the base member 302. In other words, the side walls 304 may have a longitudinal centerline and/or side surfaces engaging the surgical clip 100 disposed at the acute angle, θ, to provide the compartments 306 at the acute angle, θ, relative to the vertical axis of the base member 302. The pedestals 308 may extend at the acute angle, θ, from the base member 302 between the side walls 304. The base member 302 may have a bottom perimeter and/or bottom surface that is substantially flat. The base member 302 may include an adhesive on the bottom perimeter and/or surface to secure the cartridge 300 to a supporting surface (e.g., a table).

The surgical clips 100 may be supported by the pedestals 308 in the compartments 306. For example, each hinge portion 106 may engage a pedestal 308, and the first and second leg members 102, 104 may straddle opposing sides of the pedestal 308. The pedestals 308 may extend between adjacent side walls 304. The pedestals 308 may have a vertical axis extending at the acute angle, θ, relative to the vertical axis of the base member 302.

Thus, the side walls 304, the compartments 306, and the pedestals 308 may extend parallel at the acute angle, θ, relative to the vertical axis of the base member 302. Therefore, the surgical clips 100 may be supported in the cartridge 300 at the acute angle, θ, to facilitate loading of the clip applier 200 as discussed herein. The acute angle, θ, may be greater than 10°. For example, the acute angle, θ, may be about 20-30° for improved comfort and/or visibility of the user loading the surgical clip 200. Generally, unless otherwise indicated, the acute angle, θ, of the components of the cartridge 300 may be defined by a central vertical axis disposed at the acute angle, θ, relative to the vertical axis of the base member 302, an interior side surface disposed at the acute angle, θ, relative to the vertical axis of the base member 302, and/or a top, horizontal surface with a normal axis disposed at the acute angle, θ, relative to the vertical axis of the base member 302.

The side walls 304 may include a plurality of recessed and/or angled surfaces to further improve viewability of the surgical clip 100 in the cartridge 300 and/or loading of the clip applier 200. For example, side surfaces 312 may be recessed and/or angled to lead into one of the compartments 306 to minimize viewing obstructions into the compartment 306. The side surfaces 312 may also provide guiding surfaces that reorient the jaw members 208 toward the compartment 306 when inserted into the cartridge 300. The side surfaces 312 may be disposed at a surface angle, α, relative to the vertical axis of the side walls 304, as illustrated in FIG. 3. The surface angle, α, may be acute relative to the vertical axis of the side walls 304. For example, the surface angle, α, of the side surfaces may be defined by an axis along or parallel to the side surfaces 312 being about 5-45° relative to the vertical axis of the side walls 304. The side walls 304 may also include laterally extending shoulders 314 recessed at an acute angle in the lateral direction relative to the vertical axis of the sidewalls. The shoulders 314 may lower the corners of the side walls 304 to increase visibility of engagement of the bosses 112, 114 of the surgical clip 100 with the recesses 210 of the dip applier 200.

The base member 302 may further include a pair of longitudinal walls 310 on lateral sides of the base member 302 and a pair of rails 320 extending inside of the longitudinal walls 310 and on opposite sides of the side walls 304. The pair of rails 320 may support the retainer 350 to releasably retain the surgical clips 100 in the cartridge 300. The retainer 350 may have a full or partial periphery 360 having a pair of longitudinal portions 354 that are received on the rails 320 when the cartridge 300 is assembled. The periphery 360 may also have one or more vertical portions 362 received between the rails 320 and the longitudinal walls 310 when assembled. The periphery 360 may extend around at least a portion of the retainer 350. The longitudinal portions 354 and the rails 320 may have matching sawtooth configurations to align fingers 352 of the retainer on the angularly oriented surgical clips 100. Thus, inclined segments 356 of the longitudinal portions 354 may have a normal axis at the acute angle, θ, relative to the vertical axis of the base member 302 to orient the fingers 352 perpendicular of the angled surgical clips 100. Thus, the fingers 352 may also have a normal axis at the acute angle, θ, relative to the vertical axis of the base member 302. The upper ends of the inclined segments 356 may define apexes 358 of the longitudinal segments 354, and substantially vertical segments 359 may join adjacent inclined segments 356. Similarly, inclined segments 322 of the rails 320 may be oriented at the acute angle, θ, relative to the longitudinal axis of the base member 302 to receive the longitudinal portions 354. The upper ends of the inclined segments 322 may define apexes of the rails 320, and substantially vertical segments may join adjacent inclined segments 322.

The fingers 352 may be provided on opposing sides of the surgical clip 100 and include grooves 353 at free ends to receive the surgical clip 100 when received in the compartment. The fingers 352 deflect downward as the jaw members 208 are inserted to engage the bosses 112, 114 of the surgical clip 10. The retainer 350 may be made of a clear flexible plastic to ensure visibility of the bosses 112, 114 of the surgical clip 100 when in the compartment 306. The cartridge body 301 and the retainer 350 may each be formed of an integral plastic body, for example, through injection molding. The periphery 360 may have apertures 364 configured to receive pins 330 extending from the rails 320, to secure the retainer 350 to the cartridge body 301. Further discussion of the retention of the surgical clip 100 and/or manufacturing of the cartridge 300 can be found in U.S. Pat. No. 6,880,699, the entire disclosure of which is incorporated herein by reference.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A cartridge comprising:
  a pair of side walls separated by a compartment, the compartment being configured to receive a surgical clip;
  a base member supporting the pair of side walls, wherein the pair of side walls extend at an acute angle relative to a vertical axis of the base member, such that the cartridge retains the surgical clip at the acute angle; and
  a pedestal extending between the pair of side walls and configured to support the surgical clip, wherein the pedestal is disposed at the acute angle relative to the vertical axis of the base member.

2. The cartridge of claim 1, wherein the pair of side walls are substantially parallel.

3. The cartridge of claim 1, wherein the acute angle is greater than 10°.

4. The cartridge of claim 3, wherein the acute angle is about 20-30°.

5. The cartridge of claim 1, wherein at least one of the side walls has a surface inclined at a surface angle toward the compartment, the surface angle being acute relative to a vertical axis of the at least one of the side walls.

6. The cartridge of claim 5, wherein the surface angle is about 5-45° relative to the vertical axis of the at least one of the side walls.

7. The cartridge of claim 1, wherein the cartridge has a plurality of side walls along a longitudinal axis of the base member, and a plurality of compartments, wherein each of the plurality of compartments is between respective adjacent side walls.

8. The cartridge of claim 1, wherein the base member comprises a pair of longitudinal walls extending on opposing sides of the compartment.

9. A cartridge comprising:
- a pair of side walls separated by a compartment, the compartment being configured to receive a surgical clip;
- a base member supporting the pair of side walls, wherein the pair of side walls extend at an acute angle relative to a vertical axis of the base member, such that the cartridge retains the surgical clip at the acute angle; and
- a pair of rails extending longitudinally along the base member, wherein the pair of rails have a sawtooth configuration with inclined segments at the acute angle.

10. The cartridge of claim 9, wherein the pair of side walls are substantially parallel.

11. The cartridge of claim 9, wherein the acute angle is greater than 10°.

12. The cartridge of claim 11, wherein the acute angle is about 20-30°.

13. The cartridge of claim 9, wherein at least one of the side walls has a surface inclined at a surface angle toward the compartment, the surface angle being acute relative to a vertical axis of the at least one of the side walls.

14. The cartridge of claim 13, wherein the surface angle is about 5-45° relative to the vertical axis of the at least one of the side walls.

15. The cartridge of claim 9, wherein the base member comprises a pair of longitudinal walls extending on opposing sides of the compartment.

16. A cartridge comprising:
- a pair of side walls separated by a compartment, the compartment being configured to receive a surgical clip;
- a base member supporting the pair of side walls, wherein the pair of side walls extend at an acute angle relative to a vertical axis of the base member, such that the cartridge retains the surgical clip at the acute angle; and
- a retainer configured to retain the surgical clip in the compartment, the retainer including a pair of fingers configured to contact the surgical clip, wherein the pair of fingers are oriented at the acute angle;
- wherein the retainer further comprises a pair of longitudinal portions supporting the pair of fingers, wherein the longitudinal portions have a sawtooth configuration with inclined segments at the acute angle.

17. The cartridge of claim 16, wherein a pair of rails receive the pair of longitudinal portions of the retainer.

18. The cartridge of claim 16, wherein the pair of side walls are substantially parallel.

19. The cartridge of claim 16, wherein the acute angle is greater than 10°.

20. The cartridge of claim 19, wherein the acute angle is about 20-30°.

21. The cartridge of claim 16, wherein at least one of the side walls has a surface inclined at a surface angle toward the compartment, the surface angle being acute relative to a vertical axis of the at least one of the side walls.

22. The cartridge of claim 21, wherein the surface angle is about 5-45° relative to the vertical axis of the at least one of the side walls.

23. The cartridge of claim 16, wherein the base member comprises a pair of longitudinal walls extending on opposing sides of the compartment.

24. A cartridge comprising:
- a cartridge body including:
  - a pair of side walls separated by a compartment, the compartment being configured to receive a surgical clip,
  - a base member supporting the pair of side walls,
  - a pedestal extending between the pair of side walls and configured to support the surgical clip, and
  - a pair of rails extending longitudinally along the base member; and
- a retainer including a pair of fingers configured to contact the surgical clip, the retainer comprising a pair of longitudinal portions disposed on the pair of rails,
- wherein the pair of side walls and the pedestal extend at an acute angle relative to a vertical axis of the base member, such that the cartridge retains the surgical clip at the acute angle.

25. The cartridge of claim 24, wherein the pair of side walls are substantially parallel.

26. The cartridge of claim 24, wherein the acute angle is greater than 10°.

27. The cartridge of claim 26, wherein the acute angle is about 20-30°.

28. The cartridge of claim 24, wherein the pair of rails have a sawtooth configuration with inclined segments at the acute angle.

29. The cartridge of claim 24, wherein the pair of fingers are oriented at the acute angle.

30. The cartridge of claim 24, wherein the longitudinal portions have a sawtooth configuration having inclined segments at the acute angle.

* * * * *